United States Patent [19]
Curtis

[11] 4,182,739
[45] Jan. 8, 1980

[54] BLOOD OXYGENATOR

[75] Inventor: Robert M. Curtis, Laguna Niguel, Calif.

[73] Assignee: Shiley Incorporated, Irvine, Calif.

[21] Appl. No.: 868,168

[22] Filed: Jan. 9, 1978

Related U.S. Application Data

[63] Continuation-in-part of Ser. No. 655,039, Feb. 3, 1976, Pat. No. 4,067,696.

[51] Int. Cl.$^2$ .............................................. A61M 1/03
[52] U.S. Cl. ............................. 422/47; 128/DIG. 3; 435/283; 435/2
[58] Field of Search ............... 23/258.5 A, 258.5 B, 23/258.5 BA, 258.5 M, 258.5 MH; 128/DIG. 3; 261/DIG. 28; 195/1.8; 422/45, 46, 47, 48

[56] References Cited

U.S. PATENT DOCUMENTS

| | | | |
|---|---|---|---|
| 2,771,998 | 11/1956 | Holden | 261/76 |
| 2,833,279 | 5/1958 | Gollan | 23/258.5 B |
| 3,171,820 | 3/1965 | Volz | 261/94 X |
| 3,322,411 | 5/1967 | Moore | 261/DIG. 26 |
| 3,374,066 | 3/1968 | Farrant | 23/258.5 B |
| 3,388,868 | 6/1968 | Watson et al. | 23/258.5 BH |
| 3,413,095 | 11/1968 | Bramson | 23/258.5 M |
| 3,468,631 | 9/1969 | Raible et al. | 23/258.5 BH |
| 3,468,631 | 9/1969 | Raible et al. | 23/258.5 BH |
| 3,547,591 | 12/1970 | Torres | 23/258.5 BH |
| 3,578,411 | 5/1971 | Bentley | 23/258.5 BH |
| 3,729,377 | 4/1973 | Leonard | 23/258.5 B |
| 3,769,162 | 10/1973 | Brumfield | 23/258.5 |
| 3,769,163 | 10/1973 | Brumfield | 23/258.5 BH |
| 3,807,958 | 4/1974 | Brumfield et al. | 23/258.5 |
| 3,827,860 | 8/1974 | Burlis | 23/258.5 B |
| 3,870,470 | 3/1975 | Yoshida | 23/258.5 |
| 3,898,045 | 8/1975 | Bowley | 23/258.5 |
| 3,994,689 | 11/1976 | DeWall | 23/258.5 |
| 3,998,593 | 12/1976 | Yoshida et al. | 23/258.5 MH |
| 4,058,369 | 11/1977 | Bentley et al. | 23/258.5 B |
| 4,065,264 | 12/1977 | Lewin | 23/258.5 BH |
| 4,067,696 | 1/1978 | Curtis | 23/258.5 B |

FOREIGN PATENT DOCUMENTS

| | | | |
|---|---|---|---|
| 1089125 | 9/1960 | Fed. Rep. of Germany | 23/258.5 |
| 2315283 | 1/1977 | France | 23/258.5 BH |
| 715612 | 9/1954 | United Kingdom | 422/45 |
| 302125 | of 1971 | U.S.S.R. | 23/258.5 |

OTHER PUBLICATIONS

DeWall et al., Theme and Variation on Blood Oxygenators, Surgery, Dec. 1961, p. 931.
Hempel, H. W., Design of Artificial Lung Using Polyvinyl Formal Sponge Lance Dec. 1956, p. 1246.
Bencini et al., Preliminary Studies on the Sponge Oxygenators, Surgery, Aug. 1957, p. 342.
Shiley S-100 Oxygenator, Sales Brochure & Operating Instructions.

*Primary Examiner*—Michael S. Marcus
*Attorney, Agent, or Firm*—Knobbe, Martens, Olson, Hubbard and Bear

[57] ABSTRACT

A blood oxygenator wherein blood and oxygen are admixed by flowing blood, into which has been introduced bubbles of oxygen, through a three-dimensional, open cellular mixing material having a substantial void volume. The resulting arterialized blood and blood foam rise to the top of the admixing chamber and are contained in a channel located at the top of the chamber and directed through this channel to the input of a defoamer chamber. A defoamer filter of annular configuration is retained within the defoamer chamber such that the defoamer inlet is located at the top of the defoamer filter within the interior annular space thereof. The blood foam thus enters the interior of the defoamer filter and is distributed over a substantial portion of the defoamer surface and collapsed therein to remove substantially all entrapped gases. The oxygenated defoamed blood collects at the bottom of the defoamer chamber for return to the patient's body. In the preferred embodiment, the defoamer chamber is provided with an unobstructed annular defoamer filter inlet opening for enhanced contacting of the defoaming material by the blood and blood foam while minimizing blood hemolysis, and an integral vent which permits the entrapped gases to be exhausted from the oxygenator either by free flow or by a vacuum source.

11 Claims, 14 Drawing Figures

BLOOD OXYGENATOR

CROSS REFERENCE TO RELATED APPLICATION

This is a Continuation-In-Part of co-pending Application Ser. No. 655,039, filed Feb. 3, 1976, now U.S. Pat. No. 4,067,696.

BACKGROUND OF THE INVENTION

Extracorporeal circulation is and has been a routine procedure in the operating room for several years. An important component in providing extracorporeal circulation is the blood oxygenator. The function of the oxygenator is to place oxygen in close relationship to the venous blood such that the oxygen reacts with the hemoglobin with resultant absorption of the oxygen and release of carbon dioxide. For an interesting historical survey of blood oxygenators see the article published in the December, 1961 issue of Surgery entitled "Theme and Variations of Blood Oxygenators" by Richard A. DeWall, M.D., et al.

Three principal types of blood oxygenators are known in the art:

1. In the membrane oxygenator, a membrane separates the blood from the oxygen and gas exchange takes place by diffusion through the membrane. One type of membrane oxygenator is described in U.S. Pat. No. 3,413,095—Branson.

2. A film oxygenator exposes a thin film of blood to an oxygen atmosphere. One type of film oxygenator is described in the Dec. 15, 1956 issue of *The Lancet*, page 1246 in the article entitled "Design of an Artificial Lung Using Polyvinyl Formal Sponge".

3. The bubble oxygenator introduces bubbles of oxygen directly into the blood. In the bubble oxygenator described in U.S. Pat. No. 3,578,411, the bubble chamber has a continuous convoluted path to promote the intermixing of the blood and oxygen. U.S. Pat. No. 3,807,958 describes a bubble oxygenator which employs a plurality of vertical tubes through which the blood and oxygen mixture rises in a slug flow. U.S. Pat. No. 3,898,045 describes a bubble oxygenator having a lattice chamber tightly packed with spherical beads to provide what the patentee describes as a "wiped film bubble oxygenation process". In still another type of bubble oxygenator described in an article published in Surgery, August, 1957 entitled "Preliminary Studies On the Sponge-Oxygenator" by Adriano Bencini, M.D., et al, a long multi-perforated needle is inserted into a cylindrical piece of polyurethane sponge.

The oxygen used in blood oxygenators is quite often mixed with an anesthesia gas. In those states and foreign countries which have laws prohibiting the open venting of anesthesia gas, it is necessary to remove this gas mixture from the oxygenator by means of a vacuum source. To this end, various types of gas venting configurations have been developed to allow a vacuum exhaust without imparting a negative pressure to the interior of the oxygenator. To date, such gas vents have been in the form of separate components which are attached to the oxygenator when needed.

SUMMARY OF THE INVENTION

The present invention relates to an improved type of "sponge" oxygenator as taught by Dr. Bencini et al, supra.

In the preferred embodiment as described hereinafter, the admixing chamber is formed by an upright plastic cylinder. The oxygen is introduced at the bottom of this cylinder and is caused to form a plurality of oxygen bubbles by means of a sparger. These bubbles flow through venous blood which enters a cylindrical chamber in the cylinder above the sparger. This venous blood into which the bubbles of oxygen gas have been introduced then flows upwardly through a three-dimensional, open cellular mixing material having a substantial void volume completely filling the open cross-sectional area of the admixing chamber along the length of the mixing material. This mixing material thoroughly mixes the gaseous oxygen and liquid blood phases and produces a large quantity of blood foam. As a result, $CO_2$ is removed from the blood and the blood is saturated with oxygen.

The arterialized blood and blood foam flow out of the top of the admixing chamber and are contained in a channel connected to the inlet of a defoamer chamber. The defoamer chamber likewise advantageously comprises a second upright plastic cylinder having mounted therein an annular defoamer filter. The blood and blood foam enter the interior of the annular defoamer filter through a uniform, continuous unobstructed annular inlet which causes the blood to cascade down in close adherence with the exterior surface of an inner cylindrical column. As a result, a substantial portion of the interior cavity wall surface of the defoamer filter is contacted by the arterialized blood and blood foam. The defoamer filter collapses the bubbles in the blood such that the entrapped gases escape through openings formed in the defoamer chamber. The arterialized whole blood falls to the bottom of the defoamer chamber from which it is returned to the patient. In the preferred embodiment, the defoamer chamber has an integral gas vent which permits these entrapped gases to be removed from the defoamer chamber either by free flow or by an external vacuum source.

A significant feature of this invention is that it requires a low rate of oxygen flow, i.e., saturation of the blood with oxygen and the concomitant removal of $CO_2$ are achieved with a low volumetric ratio of oxygen to blood. Thus, certain types of bubble oxygenators in wide usage require between two and two and one-half liters of oxygen for each liter of venous blood at atmospheric pressure. The present invention operates very efficiently and satisfactorily on approximately one liter or less of gas to one liter of blood ratio at atmospheric pressure. Such a low rate of oxygen flow is deemed important because published technical papers report that the degree of blood trauma in bubble oxygenators can be related to the volumetric ratio of oxygen to blood.

Although all aspects of the improved blood oxygenation provided by the invention are not presently known, it is believed that one reason that oxygen saturation and $CO_2$ removal are achieved with a relatively low rate of oxygen flow is that the mixing and churning of the blood and bubbles of oxygen within the three-dimensional open cellular mixing material produces a substantial disturbance to the diffusion boundary layers occurring at the surfaces of the oxygen bubbles. This mixing activity is further enhanced in that the oxygen bubbles are broken down in size and forced to take tortuous paths through the blood. The thorough mixing of blood and oxygen bubbles achieved in this invention is physically manifested by the production of large numbers of small bubbles, the mixture of blood and bubbles exhibiting a foam-like behavior and referred to below as blood foam. As described hereinafter, oxygenators constructed in accordance with this invention effectively channel and collapse substantially all of the foam produced during admixing of the blood and oxygen.

The conventional teaching of the prior art in the field of bubble and other types of blood oxygenators as exemplified by the paper of Dr. Bencini et al, supra, was that blood foaming should be avoided or at least minimized. The present invention is therefore a substantial departure from and quite distinctive over the prior art blood oxygenator including both bubble and film-type devices since the present invention is designed to and does promote the formation of blood foam. Extensive animal testing of bubble oxygenators constructed in accordance with this invention employing standard oxygenator test procedures proved that the invention achieves saturation of the blood with oxygen and removal of $CO_2$ therefrom with significantly low rates of oxygen flow while maintaining the blood integrity to the same or higher standards as contemporary bubble oxygenators.

A correlative advantage of the admixing chamber of the present invention is that the mixing material therein advantageously has a substantial void volume. As a result the blood is not required to pass through any constricted spaces. The admixing chamber is therefore a low impedance to the flow of blood and in addition the blood flow velocity within the admixing chamber is kept low. As a result, no positive pressure source and only gravity feed from the patient is required on the venous inlet side of the device.

Other features of the invention are that it is sufficiently inexpensive to manufacture such as that it can be a disposable item thereby avoiding any necessity to sterilize the unit after use. The individual components of the oxygenator are easily and inexpensively manufactured from materials which are biologically inactive and compatible with human blood.

DETAILED DESCRIPTION OF THE INVENTION

Figure 1:
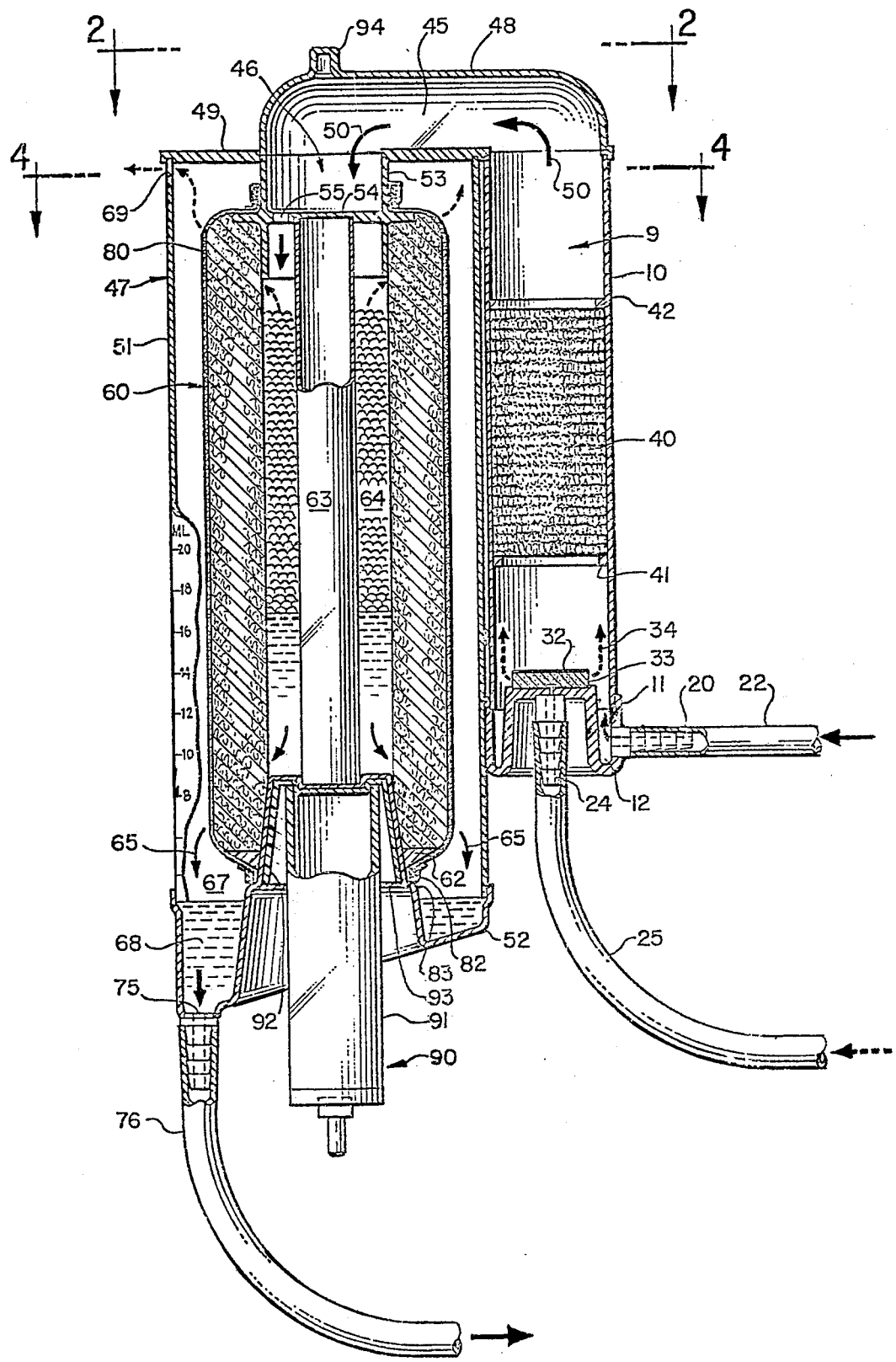
FIG. 1 is a vertical elevational partial sectional view of a blood oxygenator constructed in accordance with the present invention.
Figure 2:
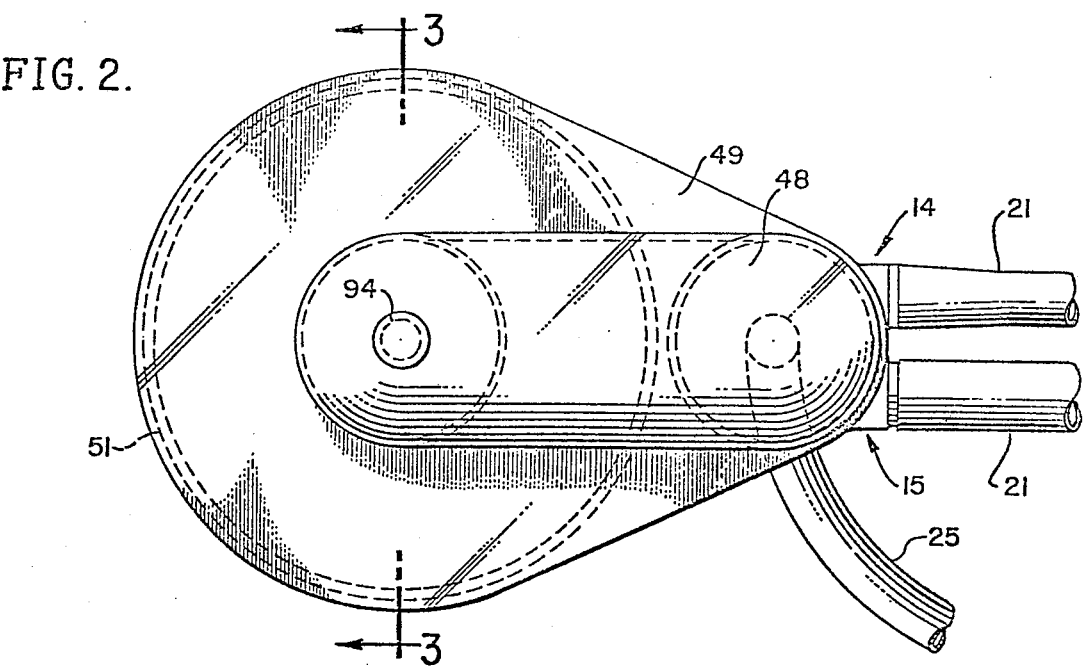
FIG. 2 is a top elevational view of the blood oxygenator.
Figure 3:
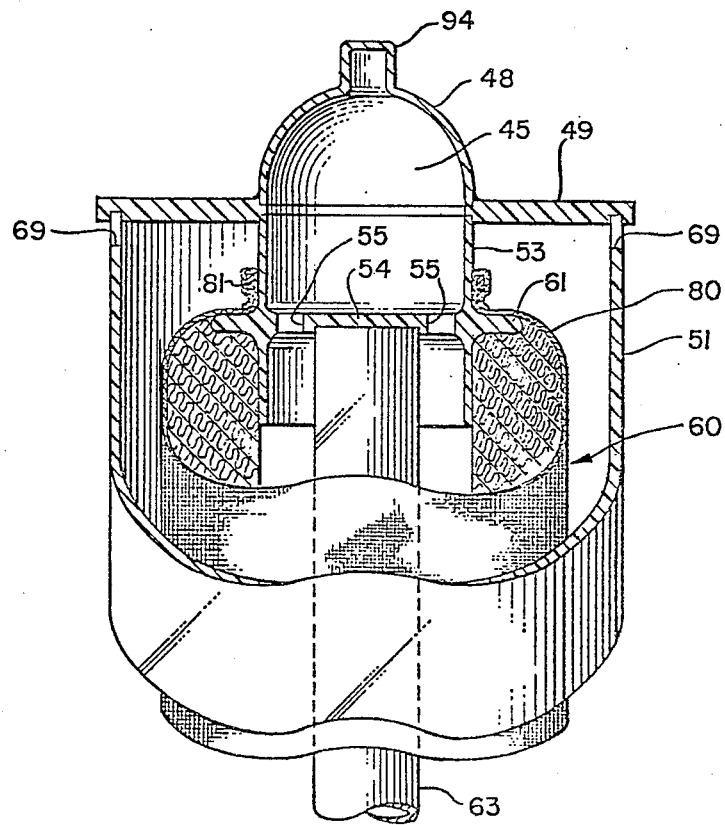
FIG. 3 is a partially sectional view taken along the line 3—3 of FIG. 2 and shows the internal construction of the defoamer filter.
Figure 4:
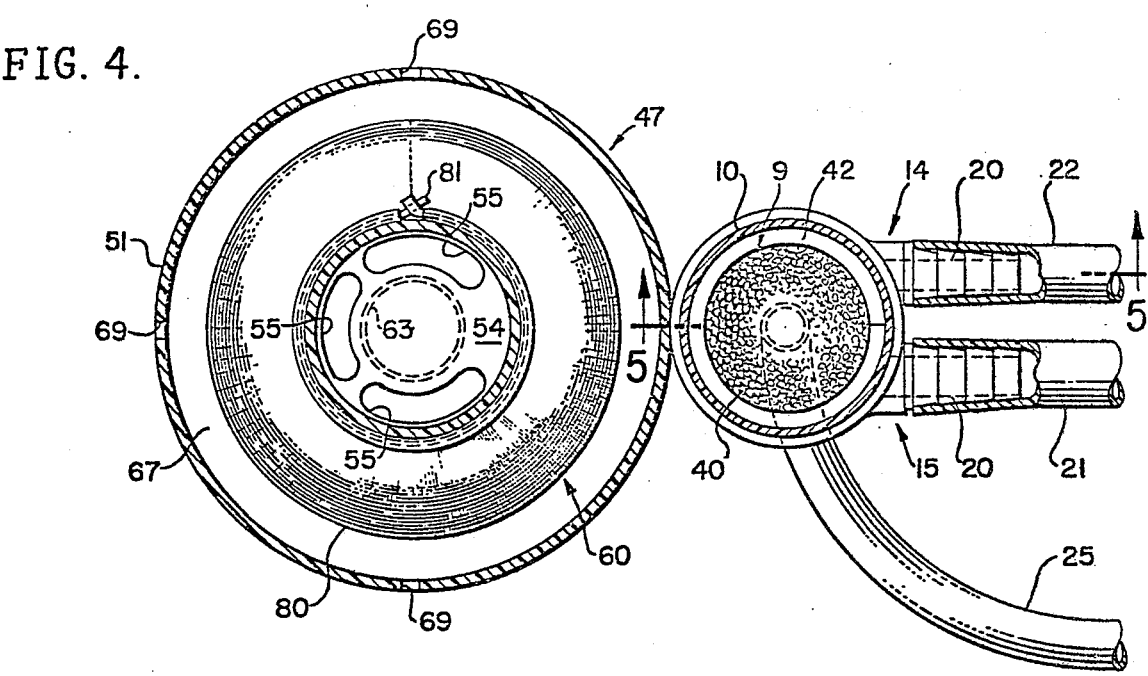
FIG. 4 is a horizontal sectional view taken along the line 4—4 of FIG. 1 and shows structural details of the admixing chamber and the defoamer filter.
Figure 5:
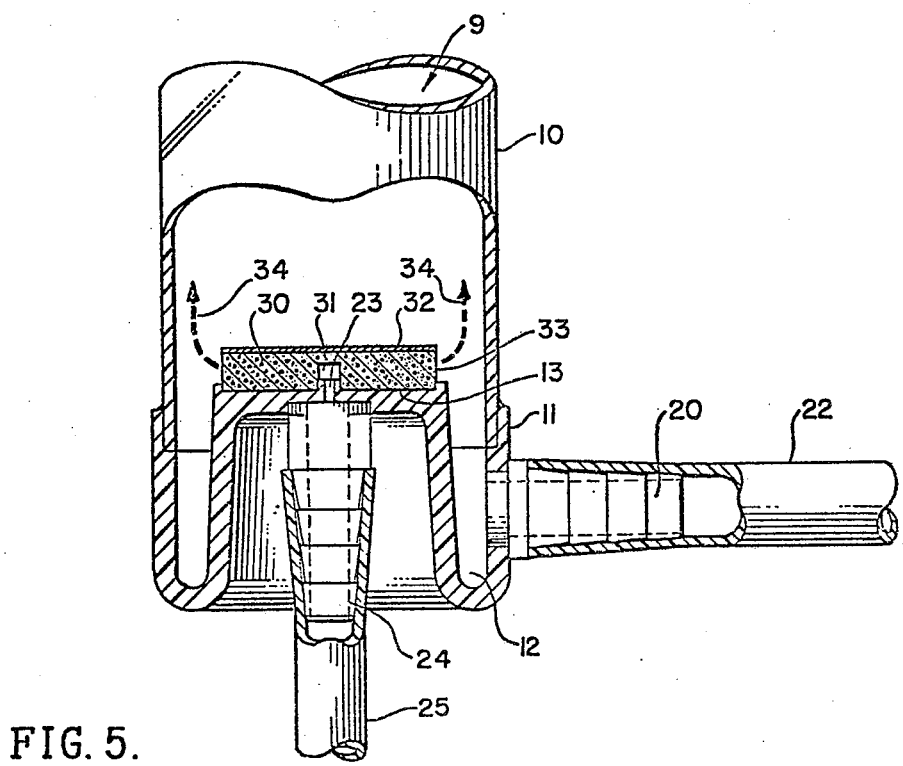
FIG. 5 is an enlarged partially sectional view taken along the line 5—5 of FIG. 4 and shows the details of the oxygen and venous blood inlets and sparger assembly.

Referring now to FIGS. 1-5, the blood oxygenator includes an oxygenating chamber 9 for thoroughly admixing blood and oxygen. In the embodiment shown, this chamber 9 is formed by a cylindrical shell 10 having its lower end closed off by a multi-port end cap 11. As particularly shown in FIG. 5 this end cap is configured to form an annular interior trough 12 surrounding a raised horizontal surface 13. In the outer wall of the end cap 11 are formed one or more blood inlet ports. As shown in FIGS. 2 and 4, two such ports 14,15 are advantageously provided one to be connected to a venous drain from the patient and the other to be connected to a cardiotomy reservoir supplied with blood evacuated from the surgical site. Each of these ports 14 and 15 advantageously includes a ridged inlet connector 20 for facilitating attachment to the flexible venous blood conduits 21 and 22. In the center of the cap 11 and extending through the horizontal wall 13 is an oxygen inlet port 23 also advantageously including an outwardly extending ridged connector 24 for attachment to a flexible oxygen line 25.

In use, venous blood enters the ports 14,15 under a sufficient head of pressure to cause the blood to flow through the oxygenator. Typically this pressure is provided by mounting the entire oxygenator assembly below the patient.

The oxygen entering the inlet port 23 is advantageously caused to form a plurality of oxygen bubbles by means of a sparger 30 which advantageously comprises a solid disc of Tegraglas, a material formed from a multiple of densely packed glass beads of the order of 0.040 cm in diameter and available from the 3M Company. A central plenum chamber 31 is formed in the underside of the sparger disc 30 in communication with the port 23 and a coating 32 of sealant is applied to the top surface of the disc as shown in FIG. 3. As a result, oxygen under pressure flows through the conduit 25, connector 24 and inlet port 23 through the multiple minute spaces provided by the closely packed glass beads to form a multiplicity of oxygen bubbles flowing out of the outer circumferential perimeter 33 of the sparger disc 30 along generally horizontal axes. These bubbles, represented by the arrows 34, flow through the venous blood entering the annular trough 12. This blood, being under pressure, rises inside the chamber 10.

Other means known in the art for forming oxygen bubbles may be used instead of the sparger 30. Moreover, the size of the bubbles produced is not critical as the bubbles are broken down in size during the admixing process. Thus, while the Tegraglas sparger used in the animal tests described in co-pending Application Ser. No. 655,039, Filed Feb. 3, 1976, produced bubbles having diameters of the order of 0.3 to 0.5 cm, larger and smaller bubble sizes may be employed in the oxygenator of this invention.

The venous blood and oxygen bubbles are thoroughly admixed as they flow through a three-dimensional, open cellular mixing material 40 supported above the sparger 30 within the chamber 9 and completely filling the cross-sectional interior of the chamber 10 along the length of the mixing material 40. The open cellular material 40 produces substantial mixing and churning together of the blood and oxygen bubbles. This mixing and churning disturbs the diffusion boundary layers which exist at the surface of the oxygen bubbles to facilitate the reaction of the oxygen with the blood hemoglobin. In addition, the mixing material 40 breaks down the bubbles produced by the sparger 30 and forces these bubbles to follow tortuous paths through the blood. It has been found that this admixing process provides an excellent and thorough admixing of the blood and oxygen and produces blood foam which emerges at the top of the open cell material 40. The open cellular material 40 is retained within the chamber 9 by a pair of annular rings 41 and 42 attached to the inner wall of the shelf 10. The degree to which the blood and oxygen are admixed is dependent upon several factors including the degree to which the blood is foamed, the thickness of the blood film forming the foam, and the residence time of the blood foam in the presence of oxygen. By way of specific example, a reticulated polyurethane foam material may be advantageously used as the open cell material 40. The type of blood foam produced by the reticulated polyurethane foam material can be selectively varied by choosing the mesh size of the foam material. The residence time of this blood foam is determined by the pore size and the length of the foam material 40. Excellent saturation of the blood with oxygen and removal of $CO_2$ can be achieved using foam materials having a pore size in the range of 5 to 35 pores per inch and varying the overall material length to maintain the necessary residence time. The reticulated foam has a very substantial void volume substantially greater than 50% and, typically 85 to 97% of the total volume, providing an admixing chamber which offers a low impedance to the flow of blood and low blood velocities therewithin. In a unit used in the animal experiments described in applicant's co-pending Application Ser. No. 655,039, filed Feb. 3, 1976, the oxygenator chamber 10 had an inside diameter of 2 inches, a wall 9 inches long, and a wall thickness of 0.060 inches. The reticulated polyurethane foam material 40 had 10–15 pores per inch and was 2 inches in height. Since substantial blood foaming within the oxygenating chamber 9 has been found to be a desirable function of the mixing material 40, the reticulated polyurethane foam is advantageously not treated with an antifoam compound.

The arterialized blood in the form of liquid blood and blood foam rises to the top of the chamber 10 and is contained in a channel 45 extending from the open top end of chamber 10 to the inlet 46 of the defoamer 47. Channel 45 is formed by a generally half cylindrical shell 48 secured to a flat cover plate 49. This flow path of the arterialized blood and blood foam is represented by the arrows 50 shown in FIG. 1, the arterialized blood and blood foam flowing generally horizontally through the channel 45 and downwardly into the defoamer 47.

Defoamer 47 includes a cylindrical shell 51 adjoining the oxygenator shell 10. The top end of shell 51 is enclosed with the cover plate 49 and its bottom end is enclosed by a cap 52 having generally the shape of an inverted cup.

The inlet 46 of the defoamer 47 is formed by a generally cylindrical member 53 secured at its upper end to the cover plate 49 and open to the channel 45. As best shown in FIGS. 3 and 4, the fluid path through member 53 is partially interrupted by a disc 54 formed orthogonal to the axis of cylinder 53. As shown in FIG. 4, disc 54 includes three arcuate apertures 55 spaced from the center of the disc 54 such that both the center portion and the portion of the disc 53 nearest the oxygenating chamber 10 are closed. As described below, the open and closed portions of the disc 54 apprpriately channel the arterialized blood and blood foam into the defoamer.

Member 53 and bottom end cap 52 also serve to support an annular defoamer filter 60. Member 53 includes an annular flange 61 over which is secured the upper end of the defoamer filter 60 (FIG. 3) and the bottom end cap 52 has a shaped annular ring 62 under which is secured the bottom end of the defoamer filter 60. A cylindrical column 63 extends between member 53 and bottom end cap 52 inside the defoamer filter 60. The respective ends of this column 63 are sealed to the member 53 and end cap 52 so that the blood flow path is completely external to the column 63. Column 63 provides additional structural rigidity and improved flow through the defoamer filter 60.

The arterialized blood and blood foam represented by arrows 50 flows through the apertures 55 into the interior annular space 64 bounded by column 63 and defoamer filter 60. The bottom of this annular space is sealed by the interior wall of the end cap 62. In use, the blood and blood foam concentrate in the portion of the inlet 46 which is nearest to the oxygenating chamber 9. In order to prevent the blood and blood foam from contacting only a limited portion of the interior wall surface of the defoamer filter, the portion of disc 54 nearest to the oxygenating chamber is closed, as shown in FIGS. 1 and 4. As a result, the blood and blood foam is more evenly distributed by the spaced arcuate apertures 55 around the entire circumference of the interior wall surface of the defoamer filter.

The majority of the liquid blood entering the interior annular space 64 is guided by the column 63 to fill up the bottom of the space 64. This liquid blood flows through the defoamer filter 60 as generally shown by arrows 64. The blood and blood foam enter at the upper end of the defoamer filter 60 so that a substantial portion of the interior wall surface of the filter 60 is contacted by the blood foam. As a result, a substantial portion of the defoamer filter 60 is used to separate the blood foam from the entrapped gas such that the foam collapses and fluid blood flows into the annular reservoir 67 between the filter 60 and the interior wall of the defoamer chamber 51 and settles at the bottom of the chamber 51 and in the end cap 52 as shown at 68. The entrapped gases—primarily oxygen and $CO_2$—which the defoamer filter 60 separates out are represented by arrows 65 and pass out of the defoamer chamber 51 through three vents 69 (FIG. 4) located near the upper end of this chamber. As a result, only whole liquid blood collects in the space 67. This oxygenated filtered whole blood passes through an outlet port 75 located in the lower-most portion of the end cap 52 and is returned to the patient via flexible arterial conduit 76.

The defoamer filter 60 is advantageously formed from a flat sheet of foam material having a pore size of 10 to 50 pores per inch and typically of the order of one-inch thick treated with a thin film of silicone composition. The sheet is folded along its center line and the two ends brought together. This member is then turned inside out to form the annular filter 60 shown in the drawings. This annular filter is covered with a fine weave filter cloth 80, one end of the filter cloth being secured around cylindrical member 53 above flange 61 by a plastic tie 81. The bottom portion of the filter cloth is likewise secured by a plastic tie 82 within the annular indentation formed by the annular ring 62 and a projecting ridge 83 formed in the end cap 52. Ties 81 and 82 also serve to physically secure the annular filter 60 to the member 53 and cap 52. Filter cloth 80 insures that any accumulated blood fragments, particles, etc., in the blood are prevented from entering the annular reservoir 67.

The volume of the defoamer filter should be capable of collapsing the foam produced during (i) the highest ratio of blood and oxygen flow used during a perfusion and (ii) the maximum possible time period of the perfusion procedure. By way of specific example, in the animal experiments described in the above-referenced co-pending Application, the defoamer was constructed from a sheet of polyurethane foam one-inch thick having 20 pores per inch. This sheet was formed into an annulus 10½ inches long supported in a cylindrical shell 51 which was 5 inches in diameter, 12 inches long, and had a wall thickness of 0.060 inches. The internal column 63 had an outside diameter of one inch.

In use, the blood oxygenator is initially primed with whole blood to compensate for the volume of blood withdrawn from the patient and maintained in circulation ex vivo during the bypass procedure. As described below, the shell 51 is advantageously formed from a clear plastic material. A graduated scale on the side of the shell 51 as shown in FIG. 1 thus permits a precise amount of priming blood to be added. In addition, the amount of blood in the defoamer chamber may be visually monitored at all times so that both excessive or insufficient blood levels in the system may be avoided.

A mounting pedestal 90 includes as shown in FIG. 1 a vertical column 91 secured to the bottom of a cup-shaped member 92 which fits into the upwardly extending portion of the end cap 52. Column 91 extends through a central aperture of a disc 93 whose perimeter is secured to the bottom edge of the cup-shaped member 92. Pedestal 90 may be in turn attached to a mounting bracket (not shown). An additional mounting bracket (not shown) may be attached to a nib 94 formed in the upper wall of the member 48.

Figure 6:
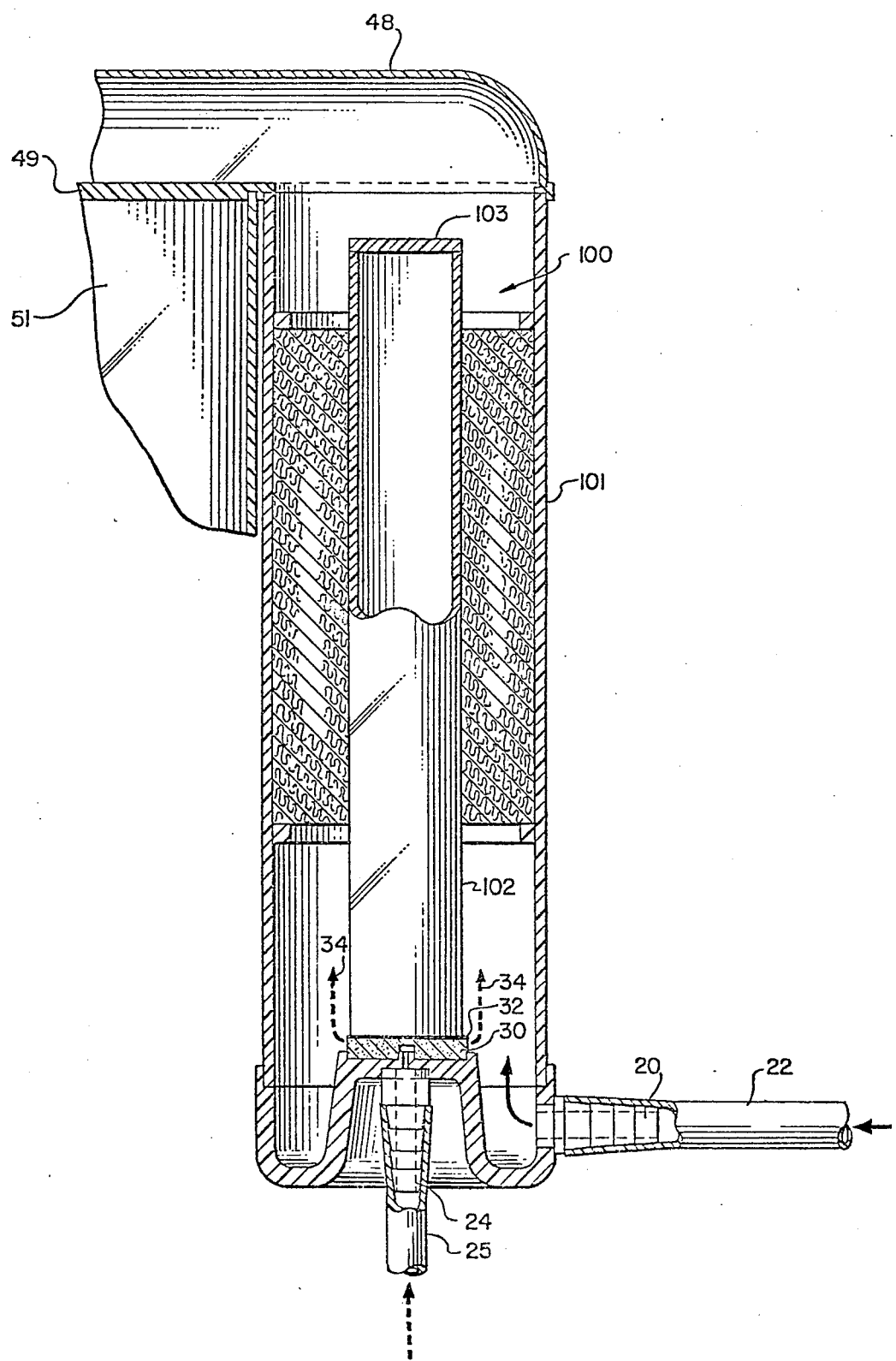
FIG. 6 is a sectional view of a modified admixing chamber which incorporates an interior cylindrical column to form an annular admixing chamber.

A modified embodiment of the oxygenator chamber is shown in FIG. 6. An oxygenating chamber 100 generally larger in diameter than the chamber 9 described above and illustrated in FIGS. 1-5 is provided by an upright cylindrical shell 101 in which is coaxially mounted a column 102. The column 102 is sealed at the top end by disc 103 and at the bottom end by attachment to the sealant coating 32 of sparger 30. Reticulated foam 104 is formed in an annular configuration around the column 102 so as to completely fill the cross-sectional annular space between the column 102 and the inside wall of the cylindrical shell 101. The volume of foam material within this modified oxygenator chamber may be made equivalent to that of the open chamber 9 of FIG. 1 by increasing the diameter of the shell 101 and/or by increasing the length of the foam material. Except for this modification to the oxygenating chamber, the remainder of the blood oxygenator is identical to that of the oxygenator described above and shown in FIGS. 1-5.

Figures 7, 8:
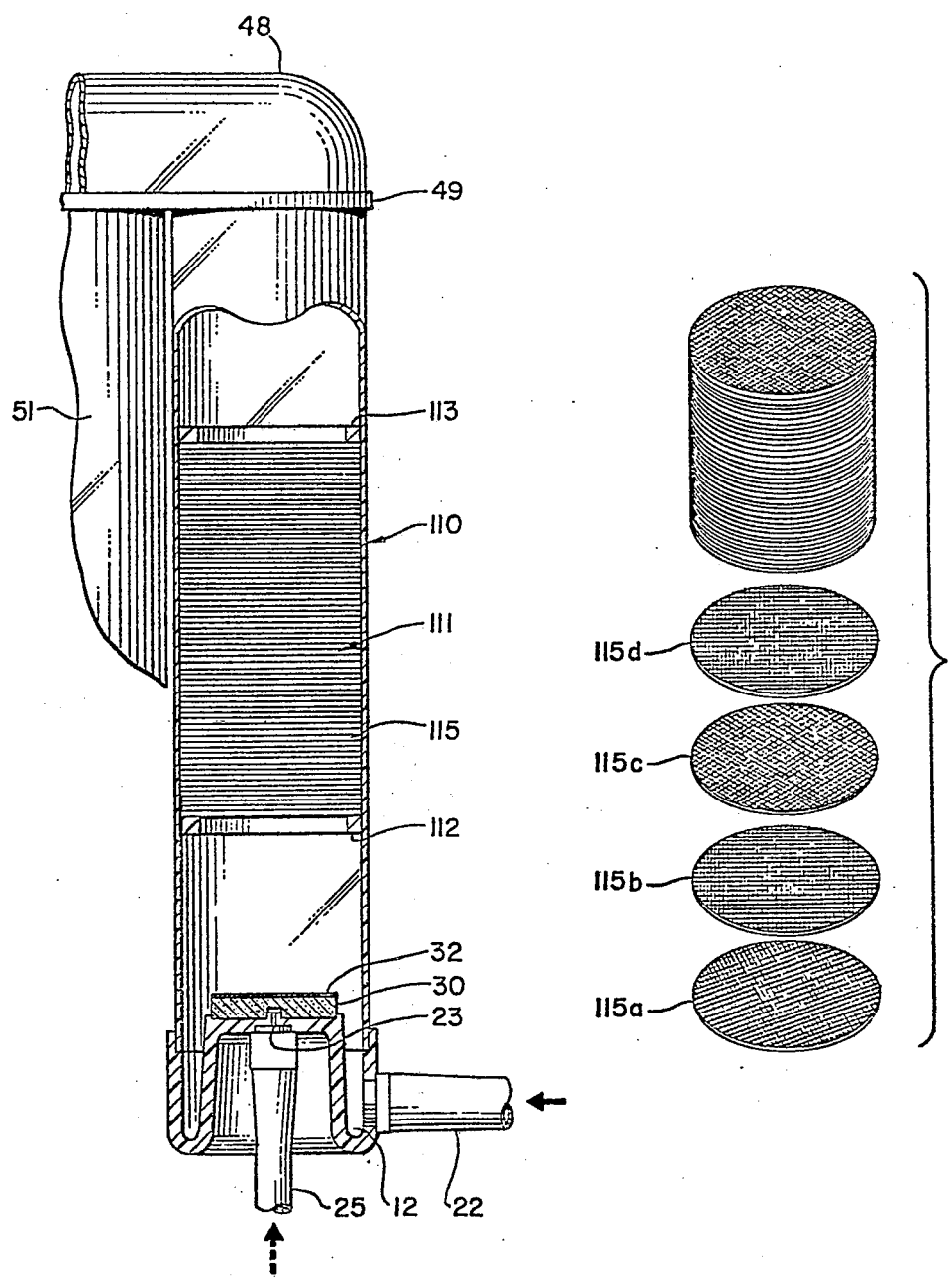
FIG. 7 is a sectional view of an alternative embodiment of the oxygenator chamber utilizing a multiple layer foraminous member.
FIG. 8 is a partially exploded view in perspective of the multiple layer foraminous admixing member shown in the embodiment of FIG. 7.
Figure 9:
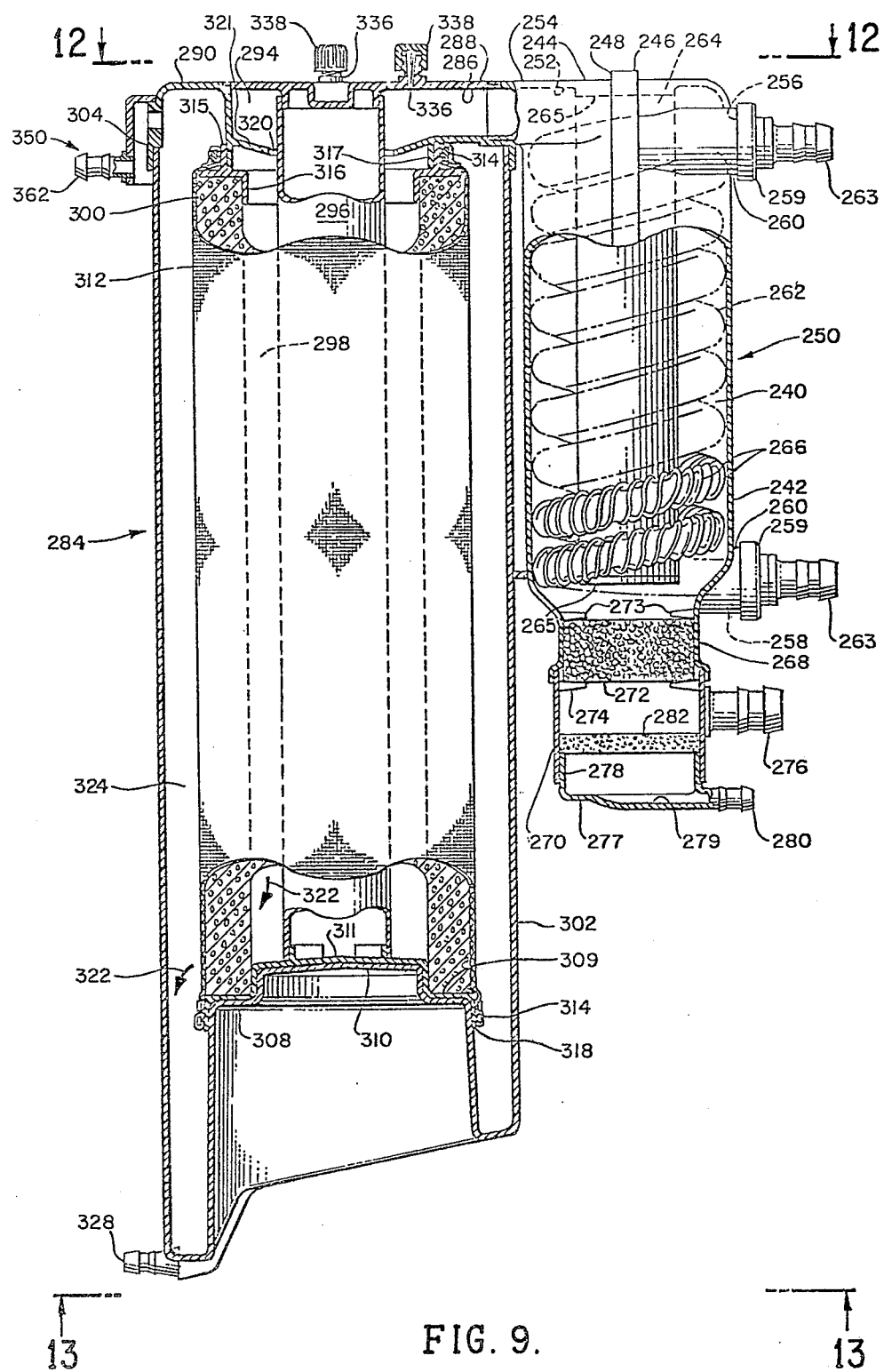
FIG. 9 is a vertical elevational sectional view of the preferred embodiment of a blood oxygenator constructed in accordance with the present invention.

An alternative embodiment of the oxygenator chamber is shown in FIGS. 7 and 8. The chamber 110 may be identical in configuration to the chamber 9 of FIG. 1. The venous blood and oxygen bubbles within chamber 110 flow through an open cell, multiple layer foraminous member 111 having a substantial void volume supported between a pair of annular rings 112,113. Member 111 is advantageously constructed by mounting a plurality of foraminous discs 115 formed from fine mesh plastic screen. As shown in FIG. 8, the axial orientation of the orthogonal plastic strands in each of the discs 115a, 115b, 115c and 115d are displaced one from the other so as to force the oxygen bubbles to follow tortuous paths through the blood. This structure also causes the oxygen bubbles to break down in size thereby providing for a thorough admixing of the oxygen and blood and production of blood foam.

The blood oxygenator of this invention may be inexpensively constructed from materials physiologically compatible with the blood. Thus, the oxygenator and defoamer cylindrical shells, end caps, and structural members in the interior of the defoamer chamber may be extruded or molded from clear polycarbonate. These members may be bonded together by known techniques including cement heat sealing, etc.

The preferred embodiment of a blood oxygenator constructed in accordance with this invention is shown in FIGS. 9 through 14. This embodiment incorporates an integral heat exchanger, as disclosed and claimed in U.S. Pat. No. 4,065,264 to Lewin. In this embodiment, the bubble oxygenating chamber 240 is formed by a pair of mating plastic shells, front shell 242 and rear shell 244. The front shell half 244 includes a grooved female peripheral flange 246, into which fits a male peripheral flange 248 on the rear shell half 242 to form a complete cylindrical shell 250. Shell halves 242 and 244 are advantageously formed by injection molding polycarbonate plastic, and may be advantageously bonded together with ethylene dichloride.

Rear shell half 244 includes a blood outlet opening 252 having an integral rearwardly extending neck 254, which is generally rectangular in cross-section. Front shell half 242 includes an upper side opening 256 and a lower side opening 258, each having an integral forwardly extending cylindrical boss 260 through which extend the respective ends of a single helically ribbed heat transfer fluid tube 262. The inside wall of these extending cylindrical bosses 260 and the proximate exterior surface of the heat exchanger tube 262 are bonded together to effect a hermetic seal. Each of the bosses 260 terminates in a tube connector 263, and redundant sealing between the bosses 260 and the heat transfer fluid tube 262 is provided by an annular sealing member 259, which may advantageously include an "O" ring (not shown).

The preferred embodiment is advantageously assembled by inserting a cylindrical extruded polycarbonate plastic interior column 264 within the helically formed ribbed tube 262. Both ends of the column 264 are hermetically sealed by end caps 265. The column 264 and the tube 262 are placed in the front shell half 242 such that the two ends of the heat exchange tube 262 extend through the openings 256 and 258. The mating shell half 244 is placed over the heat exchanger tube 262 and the mating flanges 246 and 248 are bonded together to provide a completely sealed, cylindrical shell unit 250. The peripheral portion of the ribs 266 of the tube 262 are closely proximate to and advantageously contact both the interior wall of the chamber and the exterior wall of the column 264.

The mating shells 242 and 244 are necked in at the bottom to form a hollow cylindrical neck 268. The neck 268 snugly mates with the exterior wall of a hollow, injection molded cylindrical member 270. A cylindrical layer 272 of three-dimensional, open cellular mixing material is located in the neck 268 and extends into the cylindrical member 270. The mixing material layer 272 completely fills the cross-sectional interior of the neck 268, and is supported between an upper plurality of fingers 273, extending radially inward from the inner wall of the neck 268, and a lower plurality of fingers 274 extending radially inward from the inner wall of the cylindrical member 270.

The cylindrical member 270 includes one or more blood inlet ports 276, one such port 276 being connected to the extracorporeal blood circuit by a flexible venous blood conduit (not shown).

An end cap 277 has an upwardly extending cylindrical boss 278, the exterior surface of which is bonded to the interior wall of the cylindrical member 270, thus closing off the bottom of the cylindrical member 270. A channel 279 is formed in the bottom of the end cap 278 and extends through the side thereof to form an oxygen inlet port 280 which is attached to a flexible oxygen line (not shown). The oxygen entering the inlet port 280 is caused to form a plurality of oxygen bubbles by means of a sparger 282. These bubbles flow through the venous blood entering the cylindrical member 270. The sparger 282 fills the entire cross-section of the cylindrical member 270 and rests on the upper edge of the boss 278. Alternatively, the sparger may be seated in an annular groove (not shown) in the interior wall of the cylindrical member 270. In either case, the sparger 282 is sealed around its periphery of the inner wall of the cylindrical member 270.

The blood and the oxygen bubbles then rise into the oxygenating chamber 240, where they contact the exterior of the tube 262. The combination of the tube ribbing 266 and the contacting surfaces of the cylinder 264 and the chamber 240 confine the flow of blood and oxygen bubbles substantially within paths of restricted area and extended length provided by the ribbing, thus providing a tortuous path for the blood and oxygen bubbles which, in combination with the mixing material layer 272, effects a thorough mixing thereof, resulting in a substantially complete transfer of oxygen into the blood and removal of carbon dioxide from the blood.

The arterialized blood, in the form of blood and blood foam, then flows out of the oxygenating chamber through the outlet opening 252 and the rectangular cross-section neck 254 into a defoamer chamber 284.

Figure 12:
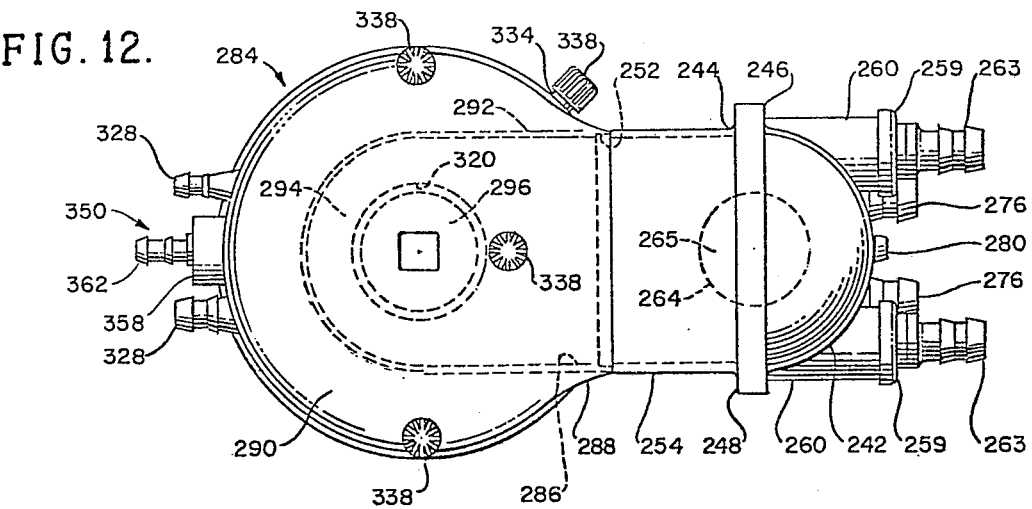
FIG. 12 is a top plan view taken along line 12—12 of FIG. 9.
Figure 13:
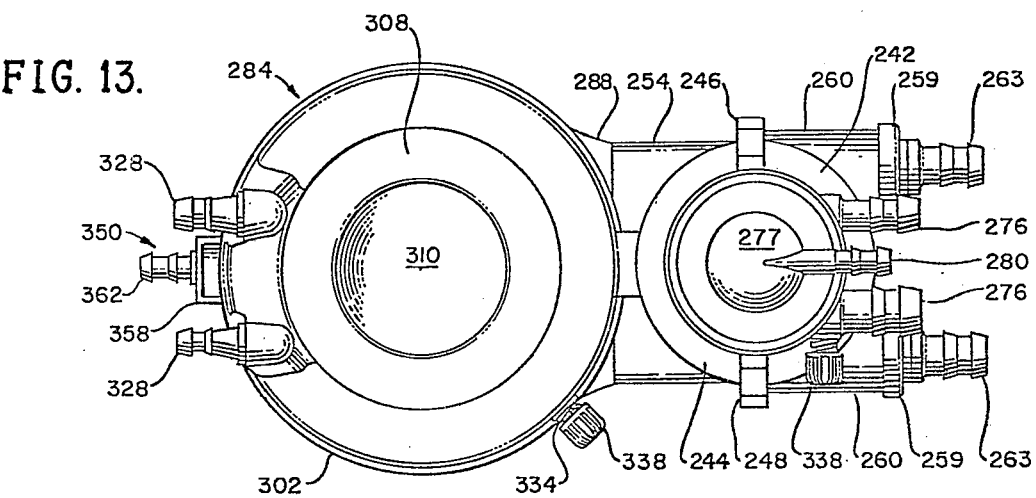
FIG. 13 is a bottom plan view taken along line 13—13 of FIG. 9.

The neck 254 communicates with a rectangular opening 286 in a rectangular cross-section boss 288 which is formed in the side of a defoamer chamber top cap 290, which is advantageously formed of injection molded polycarbonate plastic. The opening 286 in turn communicates with a fluid channel member 292 located within the top cap 290 as best shown in FIG. 12, which defines an annular defoamer inlet chamber 294.

Sealingly fixed to the underside of the top cap 290 is an extruded hollow cylindrical cascade column 296 which runs through a central axial void 298 in a tubular defoamer 300. The defoamer 300 is contained within a cylindrical injection molded polycarbonate plastic defoamer shell 302 having an integral closed bottom, and which is bonded hermetically around its upper periphery to a downwardly extending peripheral flange 304 depending from the top cap 290. The bottom of the defoamer shell 302 includes an inner upwardly concave portion forming an annular seat 308 for a defoamer lower support member 309. At the inner periphery of the annular seat 308, the bottom of the defoamer shell 302 extends still further upwardly to form a circular, centrally raised portion 310. The support member 309 bends appropriately, so as to contact the inner surface of the raised portion 310 forming a circular centrally raised platform 311, the inner surface of which closes the bottom portion of the axial void 298 and seals the bottom of the cascade column 296.

As in the previously described embodiments, the defoamer 300 consists of an annular tube of reticulated porous sponge material, such as polyurethane foam, and is closed in a filter cloth 312 of nylon tricot or dacron mesh. The filter cloth 312 is secured by nylon tricot or dacron mesh. The filter cloth 312 is secured by nylon cable ties 314 to an annular upper flange 315 which extends upwardly from an annular defoamer upper support member 316, which in turn is bonded to a downwardly extending cylindrical boss 317 in the top cap 290; and a lower cylindrical flange 318 extending downwardly from the defoamer lower support member 309. Both the cloth 312 and the defoamer 300 are advantageously treated with a suitable antifoam compound.

The arterialized blood and blood foam flow from the inlet chamber 294 into the annular axial void 298 through an annular inlet 320 formed by a uniform, continuous, unobstructed annular gap between the column 296 and a generally funnel-shaped partition 321 which forms the bottom of the inlet chamber 294. The majority of liquid blood entering the void 298 is guided by the column 296 to fill up the bottom of the void 298. This liquid blood flows through the defoamer 300, as generally shown by arrows 322.

A significant feature of the continuous annular inlet 320 adjacent the column 296 is that the blood and blood foam are caused to cascade down in close adherence with the exterior surface of the column 296 with a substantially 360-degree distribution around the column 296. It has been found that this flow of blood and blood foam provides contact with a substantial portion of the interior wall surface of the defoamer 300. As a result, a substantial portion of the defoamer 300 is used to separate the blood foam from the entrapped gas such that the foam collapses and fluid blood flows into an annular reservoir 324 between the defoamer 300 and the interior wall of the defoamer chamber 284 and settles at the bottom of the chamber 284. The entrapped gas, primarily oxygen and $CO_2$, which the defoamer separates out pass out of the chamber 284 through an integral vent 350 located on the rear side of the top cap 290, described below. As a result, only whole liquid blood collects in the reservoir 324, after having been cleaned of any particulate matter, such as blood fragments and microemboli, by the filter cloth 312. The oxygenated, filtered whole blood then passes through one or more outlet ports 328 located in the lower-most portion of the defoamer shell 302 and is returned to the patient by a flexible arterial conduit (not shown).

Another feature of the continuous annular inlet 320 is that its lack of obstruction to flow of the blood and blood foam from the inlet chamber 294 into the defoamer void 298 minimizes blood hemolysis.

The defoamer chamber 284 advantageously includes externally applied indicia 330 of the volume of blood contained therein. The oxygenator may also include an externally threaded venous blood sampling port 332 proximate the venous blood inlet 276, and an arterial blood sampling port 334 in the lower portion of the defoamer chamber 284. One or more priming ports 336 may also be provided in the top cap 290. The ports 332, 334, and 336 are conveniently sealed by screw caps 338.

Figures 10, 11:
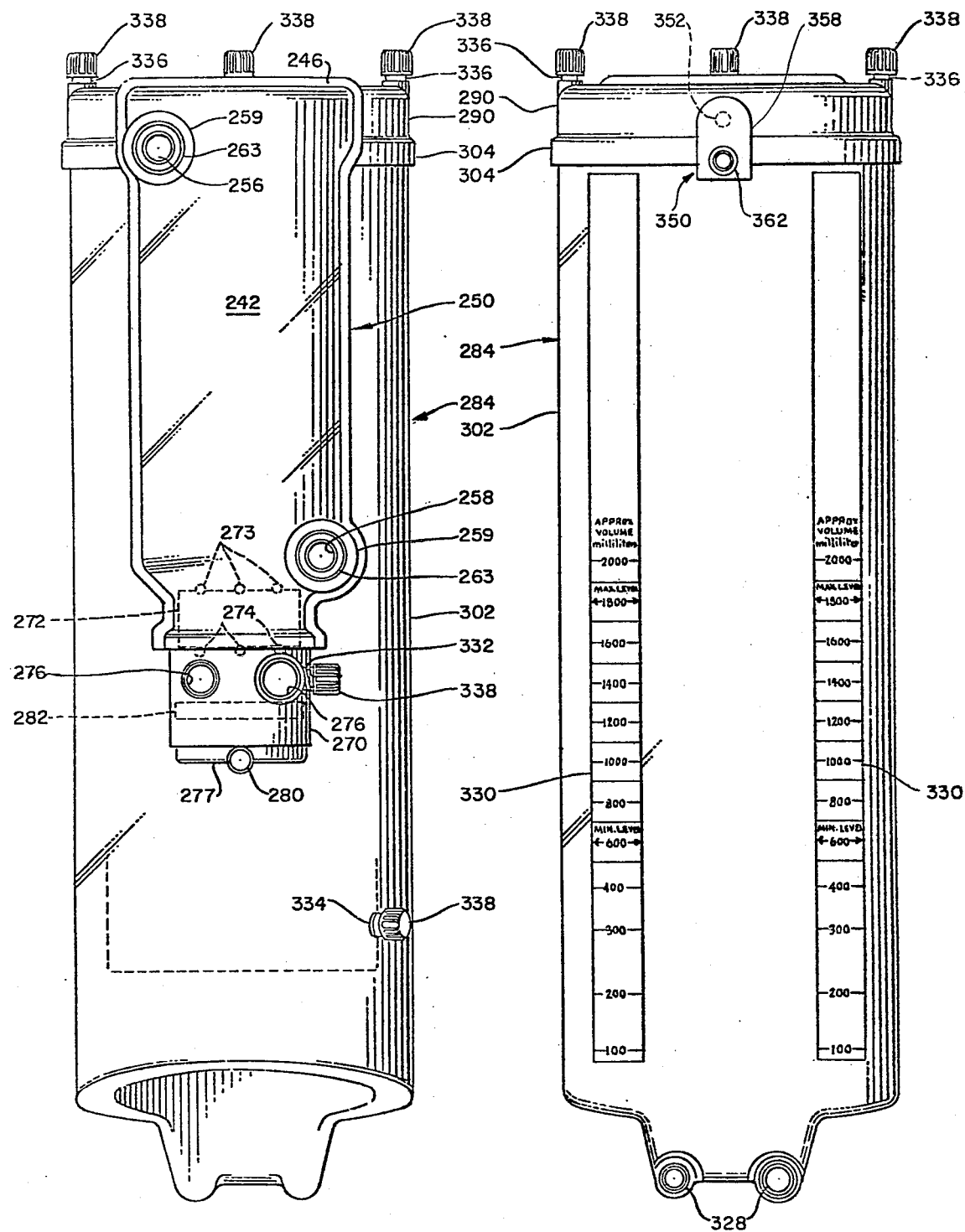
FIG. 10 is a front elevational view of the preferred embodiment of a blood oxygenator constructed in accordance with the present invention.
FIG. 11 is a rear elevational view of the preferred embodiment of a blood oxygenator constructed in accordance with the present invention.
Figure 14:
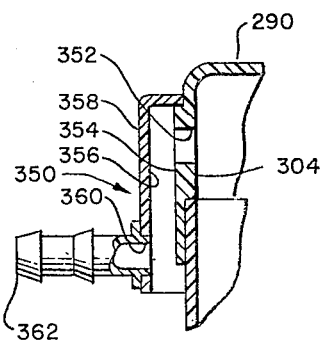
FIG. 14 is an enlarged cross-sectional view of the integral gas vent shown in FIG. 9.

As best illustrated in FIG. 14, the defoamer chamber top cap 290 is provided with an integral gas vent 350, located on the rear side of the top cap 290, as shown in FIG. 11. The vent 350 is comprised of an orifice 352 which passes through the downwardly extending flange 304 and through a flat vertical boss 354 extending outwardly from the flange 304. The orifice 352 opens into a vertical, open-bottomed channel 356 formed between the outer surface of the boss 354 and the inner surface of a downwardly extending lip 358 which is shaped in cross-section as an inverted "L", and which depends from the top cap 290 just above the juncture of the top cap and the boss 354. A gas outlet port 360 is provided in the lower portion of the lip 358, and this port is advantageously fitted with a flexible tube connector 362, to which may be attached a flexible hose (not shown) connected to an external vacuum source.

The above-described construction of the integral gas vent 350 permits the gases removed from the blood by the defoamer 300 to be exhausted from the defoamer chamber 284 in either of two ways. Normally, the gases may be allowed to flow freely out of the orifice 352 and down the channel 356 and into the ambient air in the operating room. However, in some instances, it is desirable to mix the oxygen used in blood oxygenators with an anesthesia gas, and the laws in some states and foreign countries forbid the open venting of anesthesia gas into the operating room. In the present invention, a vacuum source can be quickly and easily connected, via a flexible hose, to the tube connector 362 which communicates, through the outlet port 360 and the vertical channel 356, with the gas vent orifice 352. By properly adjusting the amount of negative pressure applied by the vacuum source, and by properly dimensioning the channel 356, orifice 352, and the outlet port 360, the vented gases can be completely exhausted by the vacuum source without substantially affecting the free flow of the gas into the channel 356, thereby preventing the imparting of any significant negative pressure to the interior of the defoamer chamber 284.

A particular advantage of the integral gas vent 350 is that it obviates the need for a separate gas vent attachment, as has heretofore been used to vent the gases released by defoamers in blood oxygenators. Such separate attachments detract from the convenience, economy, and ease of use of blood oxygenators, while these characteristics are enhanced by the use of a gas vent which is integral with the structure forming the defoamer chamber.

What is claimed is:

1. A blood oxygenator for admixing blood and oxygen for absorption of oxygen and release of carbon dioxide comprising:
   an oxygenating chamber;
   first means for introducing blood and oxygen into said oxygenating chamber comprising venous blood and oxygen inlet means therein;
   second means coupled to said oxygen inlet means for introducing a plurality of bubbles of oxygen in the venous blood;
   third means downstream of and spaced from said second means for producing substantial mixing and churning together of the blood and oxygen bubbles sufficiently to disturb the diffusion boundary layers at the surfaces of the oxygen bubbles to facilitate the reaction of the oxygen with the blood hemoglobin and characterized by the production of blood foam;
   fourth means coupled to said oxygenating chamber for containing the arterialized blood and blood foam produced by said mixing and churning;
   defoamer means for defoaming said contained blood and blood foam and producing arterialized whole blood; and
   dual mode gas venting means integral with said fourth means and in fluid communication with said defoamer means, for venting gases released by said defoamer means, and comprising:
   first venting means for allowing the free flow of said gases out of said fourth means to the ambient environment; and
   second venting means, integral with and in fluid communication with said first venting means and the ambient environment, for applying a negative pressure from an external vacuum source to said first venting means and the ambient environment without substantially affecting the free flow of said gases out of said fourth means and without imparting a significant negative pressure to the interior of said blood oxygenator, so that said gases are removed from said first venting means and from the ambient environment through said second venting means in response to said negative pressure.

2. In a blood oxygenator requiring a low volumetric ratio of oxygen to blood and having an oxygenating chamber, blood and oxygen inlet means is said oxygenating chamber, means coupled to said oxygen inlet means for introducing a plurality of oxygen bubbles in the blood, means for thoroughly mixing said oxygen bubbles with the blood and producing a blood foam, and a defoamer chamber downstream of said mixing means and containing means for defoaming the oxygenated blood by collapsing foam bubbles in the blood, thereby releasing the gas entrapped in said foam bubbles, the improvement comprising:
   gas venting means, integral with said defoamer chamber, for venting the gas released by the collapsing of said foam bubbles by said defoaming means, said gas venting means comprising:
   first venting means for allowing the free flow of said gas out of said defoamer chamber to the ambient environment; and
   second venting means, integral with and in fluid communication with said first venting means and the ambient environment for applying a negative pressure from an external vacuum source to said first venting means and the ambient environment without substantially affecting the free flow of said gas from said defoamer chamber into said first venting means and without imparting a significant negative pressure to the interior of said defoamer chamber, so that said gas is removed from said first venting means and from the ambient environment through said second venting means in response to said negative pressure.

3. A blood oxygenator for admixing blood and oxygen for absorption of oxygen and release of carbon dioxide comprising:

an oxygenating chamber;

first means for introducing blood and oxygen into said oxygenating chamber comprising venous blood and oxygen inlet means therein;

second means coupled to said oxygen inlet means for introducing a plurality of bubbles of oxygen in the venous blood;

third means for producing substantial mixing and churning together of the blood and oxygen bubbles resulting in the production of blood foam;

fourth means coupled to said oxygenating chamber for containing the arterialized blood and blood foam produced by said mixing and churning;

defoamer means for defoaming said contained blood and blood foam and producing arterialized whole blood; and dual mode gas enting means integral with said fourth means and in fluid communication with said defoamer means, for venting gases released by said defoamer means, and comprising:

first venting means for allowing the free flow of gases out of said fourth means to the ambient environment; and second venting means, integral with and in fluid communication with said first venting means and the ambient environment, for applying a negative pressure for an external vacuum source to said first venting means and the ambient environment without substantially affecting the free flow of gases out of said fourth means, and without imparting a significant negative pressure to the interior of said blood oxygenator, so that said gases are removed from said first venting means and from the ambient environment in response to said negative pressure.

4. A blood oxygenator which requires a low volumetric ratio of oxygen to blood comprising:

an oxygenating chamber;

first means for introducing blood and oxygen into said oxygenating chamber comprising blood and oxygen inlet means therein;

second means coupled to said oxygen inlet means for introducing a plurality of bubbles of oxygen in the blood, said first means providing a site for oxygen bubble formation in the absence of and unimpeded by any means for mixing said blood and oxygen bubbles;

third means so located that said blood and oxygen bubbles flows therethrough downstream of and spaced from said site for bubble formation, said third means mixing and churning together said blood and oxygen bubbles to break down said oxygen bubbles and form blood foam comprising an open cellular mixing material means within said chamber, said mixing material means having a three-dimensional body configuration for providing a plurality of tortuous paths so that oxygen bubbles are both broken down and caused to travel in a plurality of tortuous paths through said blood before escaping from said mixing material means, said three-dimensional open cellular mixing means having a void volume substantially larger than 50 percent so that said oxygenating chamber provides low impedence to the flow of blood therethrough and provides relatively low velocities of blood therein;

outlet means in said oxygenating chamber through which the oxygenated foamed blood passes;

a defoamer chamber coupled to said outlet means;

defoamer means in said defoamer chamber for defoaming the oxygenated blood by collapsing blood foam bubbles produced by said third means and releasing the gas entrapped in said foam bubbles; and gas venting means, integral with said defoamer chamber, for venting the gas released by said defoamer means, said gas venting means comprising:

first venting means for allowing the free flow of gas out of said defoamer chamber to the ambient environment; and second venting means integral with and in fluid communication with said first venting means and the ambient environment, for applying a negative pressure from an external vacuum source to said first venting means and the ambient environment without substantially affecting the free flow of said gas from said defoamer chamber into said first venting means and without imparting a significant negative pressure to the interior of said defoamer chamber, so that said gas is removed from said first venting means and from the ambient environment through said second venting means in response to said negative pressure.

5. The blood oxygenator of claim 4 wherein channel means connect the outlet means of said oxygenating chamber to said defoamer chamber, said channel means containing all of the blood foam produced in said oxygenating chamber by the mixing and churning together of the blood and oxygen bubbles.

6. The blood oxygenator of claim 5 wherein said oxygenating chamber comprises a first upright chamber and said defoamer chamber is a second upright chamber located adjacent to said first upright chamber and having an inlet means in the upper end thereof, said channel means being generally horizontal and located between the upper ends of both said first and second upright chambers and connecting the outlet means of said oxygenating chamber with the inlet means of said defoamer chamber whereby the blood and blood foam (a) flow out of the outlet means in the upper end of said oxygenating chamber into one end of said horizontal channel means, (b) flow generally horizontally from one end to the opposite end of said channel means, (c) flow from said opposite end of said channel means into the inlet means of said defoamer chamber, and (d) flow downwardly from said inlet means into said defoaming means.

7. The blood oxygenator of claim 4, wherein said defoamer means comprises:

an annular defoamer filter supported within said defoamer chamber; and defoamer inlet means connecting the upper end of said defoamer chamber with the upper end of the interior of said annular defoamer filter so that a substantial portion of the interior wall surface of the defoamer filter is contacted by the blood foam, said blood foam being collapsed in said defoamer filter with the entrapped gases passing out of an opening in the upper end of the defoamer chamber and the whole blood collected in the bottom of the defoamer chamber.

8. The blood oxygenator of claim 7 wherein said defoamer inlet means distributes the blood and blood foam around a substantial portion of the interior wall surface of said defoamer filter.

9. The blood oxygenator of claim 8, wherein said defoamer inlet means is a continuous, unobstructed annular inlet.

10. The blood oxygenator of claim 9, further comprising a rigid column extending upwardly within the interior of said annular defoamer filter, said column serving both as a support member and a guide for the liquid blood flowing into said defoamer inlet means.

11. The blood oxygenator of claim 10, wherein said annular inlet surrounds the exterior surface of said rigid column and guides the flow of blood and blood foam into a close adherence to said exterior surface substantially around the entire circumference thereof.

* * * * *